(12) United States Patent
Fontanazzi et al.

(10) Patent No.: US 9,192,709 B2
(45) Date of Patent: Nov. 24, 2015

(54) DISPOSABLE EXTRACORPOREAL BLOOD CIRCUIT AND APPARATUS FOR THE EXTRACORPOREAL TREATMENT OF BLOOD

(71) Applicant: GAMBRO LUNDIA AB, Lund (SE)

(72) Inventors: Francesco Fontanazzi, Modena (IT); Luca Caleffi, Carpi (IT); Marco Paraluppi, Medolla (IT); Giacomo Grandi, Modena (IT)

(73) Assignee: Gambro Lundia AB, Lund (SE)

( * ) Notice: Subject to any disclaimer, the term of this patent is extended or adjusted under 35 U.S.C. 154(b) by 213 days.

(21) Appl. No.: 13/865,732

(22) Filed: Apr. 18, 2013

(65) Prior Publication Data

US 2013/0292309 A1  Nov. 7, 2013

Related U.S. Application Data

(63) Continuation of application No. 12/809,035, filed as application No. PCT/IB2007/004074 on Dec. 21, 2007, now Pat. No. 8,454,553.

(51) Int. Cl.
*A61M 1/36* (2006.01)

(52) U.S. Cl.
CPC ........... *A61M 1/3621* (2013.01); *A61M 1/3627* (2013.01); *A61M 1/3687* (2013.01); *A61M 2205/12* (2013.01); *A61M 2205/123* (2013.01); *A61M 2205/331* (2013.01); *A61M 2205/3306* (2013.01); *A61M 2205/3375* (2013.01); *A61M 2209/08* (2013.01)

(58) Field of Classification Search
CPC ............ A61M 1/3621; A61M 1/3687; A61M 1/3692; A61M 1/3653; A61M 1/367; A61M 2205/3306; A61M 2205/331
See application file for complete search history.

(56) References Cited

U.S. PATENT DOCUMENTS

| | | | |
|---|---|---|---|
| 4,263,808 A | 4/1981 | Bellotti et al. | |
| 4,666,598 A | 5/1987 | Heath et al. | |
| 4,798,090 A | 1/1989 | Heath et al. | |
| 5,928,177 A | 7/1999 | Brugger et al. | |
| 6,794,194 B2 * | 9/2004 | Fava et al. | 436/66 |
| 2003/0138961 A1 | 7/2003 | Fava et al. | |
| 2004/0186416 A1 * | 9/2004 | Caleffi | 604/6.16 |
| 2005/0049539 A1 | 3/2005 | O'Hara, Jr. et al. | |
| 2005/0098500 A1 * | 5/2005 | Collins et al. | 210/645 |

FOREIGN PATENT DOCUMENTS

| | | |
|---|---|---|
| EP | 0 467 805 A1 | 1/1992 |
| IT | 01240489 B | 12/1993 |
| WO | 02/071039 A1 | 9/2002 |
| WO | 2004/082731 A2 | 9/2004 |

* cited by examiner

*Primary Examiner* — Kami A Bosworth
*Assistant Examiner* — Nilay Shah
(74) *Attorney, Agent, or Firm* — K&L Gates LLP

(57) ABSTRACT

A rigid tubular piece and a cassette assembly for extracorporeal blood circulation having the rigid tubular piece are disclosed. The rigid tubular piece is used for submitting fluid circulating therein to measurements and includes a protrusion or a recess in correspondence of at least an end connector. A blood treatment medical apparatus using the cassette assembly is also disclosed. The apparatus is able to detect if the right rigid tubular piece is in proper position before authorizing measurements of a blood property.

19 Claims, 10 Drawing Sheets

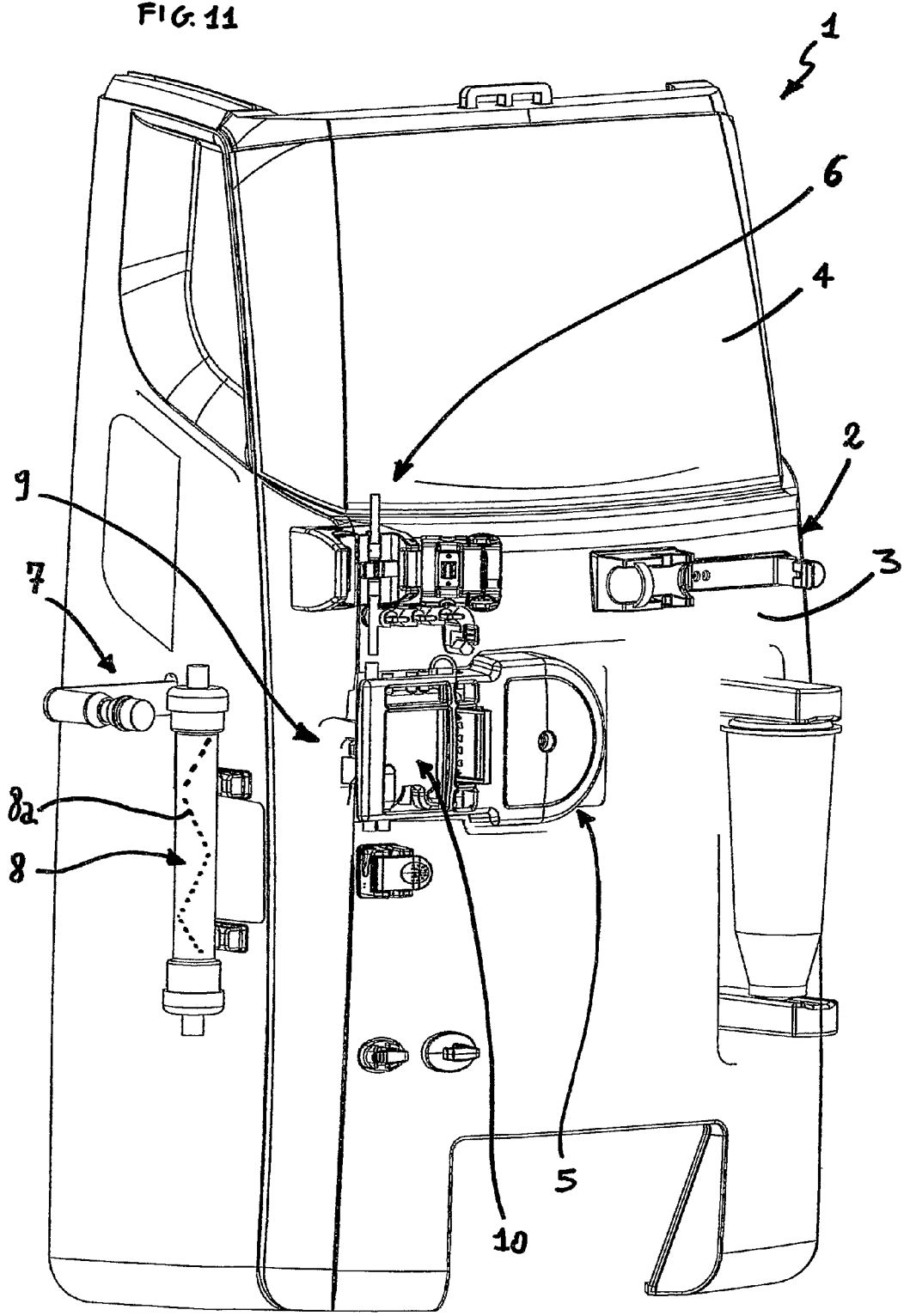

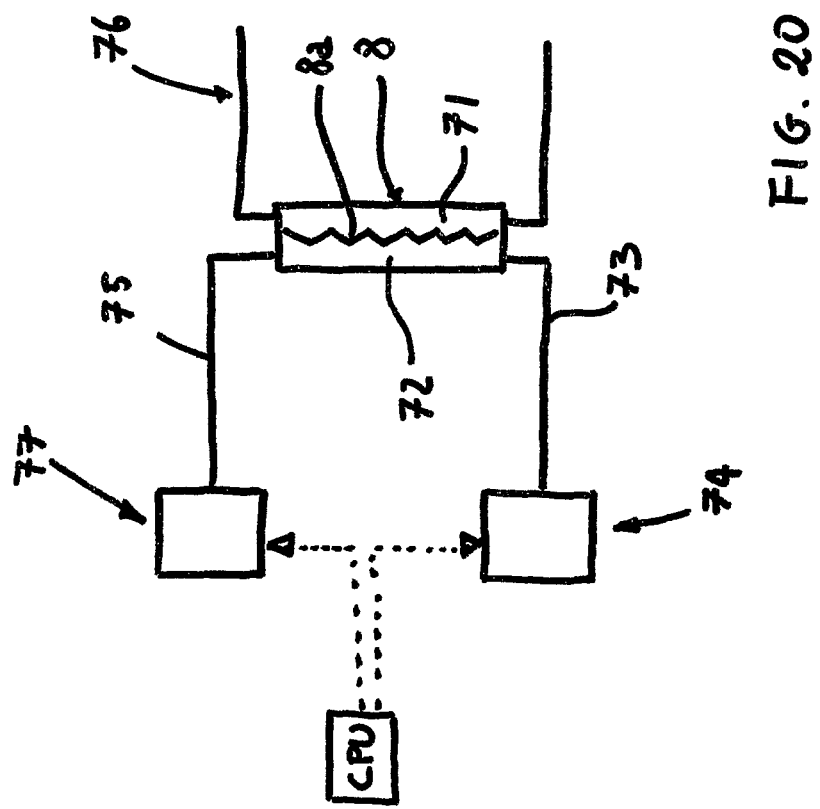

DISPOSABLE EXTRACORPOREAL BLOOD CIRCUIT AND APPARATUS FOR THE EXTRACORPOREAL TREATMENT OF BLOOD

FIELD OF THE INVENTION

The invention relates to a disposable extracorporeal blood circuit and to an apparatus for the extracorporeal treatment of blood adapted to use said extracorporeal blood circuit.

BACKGROUND OF THE INVENTION

Extracorporeal blood circuits are use to move blood outside the body: blood is typically pumped through tubes and arterial and venous bubble traps of disposable tubing sets connecting the patient to a blood treatment unit, for instance a dialyzer mounted on a dialysis, or to a treatment unit of another type (hemofilter, ultrafilter, hemodiafilter, plasmafilter, etcetera) associated to a corresponding blood treatment machine.

Integrated solutions have been used to ease the machine set-up before treatment starts.

U.S. Pat. No. 4,263,808 discloses, a one-piece circuit that includes arterial and venous bubble trap chambers in which blood enters at entrances above the bottoms of the chambers and leaves near the bottoms of the chambers. Pressure in the chambers can be determined by transducers placed against impermeable latex membranes covering holes communicating with upper portions of the chambers.

U.S. Pat. Nos. 4,798,090 and 4,666,598 disclose a one-piece fluid flow chamber cassette that can be mounted against a supporting machine. The cassette has a flexible tube that extends from a sidewall and forms a loop that is symmetrical about a loop axis that is transverse to the sidewall so that the loop will be acted upon by a pump roller on the machine when the front wall is against the machine. The flexible tube is connected at one end to a chamber outlet at the bottom of the chamber and at the other end to the inlet of a flow passage in the cassette, which inlet is located at the same distance from the loop axis as the chamber outlet; the cassette has two chambers (arterial and venous chambers) and additional flexible tubes for connecting a dialyzer between the flow passage and the venous chamber; the outlet of the venous chamber is at the bottom of the venous chamber; and the inlets to the arterial and venous chambers enter the arterial and venous chambers at locations above the outlets of the chambers. In use with a dialyzer, blood from a patient flows through the arterial chamber, the pump loop, and the flow passage to the dialyzer, and from there through the venous chamber and back to the patient.

It is also known measuring haemoglobin concentration in the blood circuit of a dialysis machine: a known way of determining the concentration of haemoglobin in the red corpuscles during the dialysis treatment, by means of highly accurate measurements of an intrusive kind, which require the laboratory examination of blood samples.

Other dialysis machines enable non-intrusive measurements of the haemoglobin concentration to be made within the machine. The non-intrusive measurements made within the machine are less accurate than laboratory measurements, but have the advantage of being provided in real time in such a way that the operating parameters of the dialysis machine can be corrected instantaneously. Italian patent IT 1240489 discloses a method of measuring the haemoglobin concentration within the machine and in a non-intrusive way, by measuring the absorption of electromagnetic waves of the blood flowing in the arterial branch of the first circuit.

In order to implement this method a blood circuit, having an arterial line, a venous line and a bubble trap in the arterial line, also included a calibrated and rigid piece of transparent tube is rigidly engaged at the outlet of the bubble trap, upstream the connection to the dialyzer. This calibrated piece of transparent tube was designed to be received in an appropriate holder where an emitter and sensor operated to emit and then detect the absorption of electromagnetic waves.

U.S. Pat. No. 6,794,194 discloses another method for measuring the hemoglobin concentration in an extracorporeal blood circuit of a dialysis machine comprising the measurement of the values of absorption by blood of electromagnetic waves conveyed along a section of the said circuit; then the calculation of the hemoglobin concentration is made as a function of the values of absorption and the measured value of blood pressure, blood temperature and the rate of flow of the blood along the aforesaid section.

According to this method a rigid piece of calibrated and transparent tube also including a pressure transducer is interposed between the blood pump and the dialyzer in correspondence of the arterial line, in a position where an electromagnetic waves sensor and a pressure sensor both borne by the machine operate.

It is also known to use the measure of haemoglobin concentration as a parameter to control the fluid removal from blood. For instance the ultrafiltration rate can be controlled by measuring the blood haemoglobin concentration upstream the treatment unit and by keeping said haemoglobin concentration or a parameter function of haemoglobin concentration (such as the filtration factor within a range of acceptability during treatment.

Finally EP0467805 shows a blood treatment apparatus having an optical/electronic system comprising an LED diode and a photosensitive sensor capable of receiving the light radiation emitted by the LED and of providing a corresponding electrical signal. A circuit for processing this electrical signal is able to discriminate when in use a tube through which blood flows is placed between LED diode and sensor. The equipment is provided with a test circuit to check that the parts of the equipment itself are properly operating.

SUMMARY OF THE INVENTION

It is an object of the present invention to render available a disposable cassette assembly bearing a blood pump segment and having associated therewith a piece of tubing designed to render the measurement of a parameter, for instance haemoglobin concentration, reliable and repeatable.

A further object of the invention is a disposable cassette assembly, which is so designed as to isolate the portion of the tube subject to measurements from the perturbations coming from actuators acting on the blood pump segment.

An auxiliary object of the invention is a disposable cassette assembly where the tube piece designed to be subject to measurements is provided with appropriate means allowing proper positioning and identification of the tube piece so as to avoid that tubes unsuitable to the measurement are used.

According to one embodiment, the disposable cassette assembly is able to trigger generation of a consent signal for the haemoglobin concentration or related parameter measurement to take place.

According to the present invention the disposable cassette assembly for an extracorporeal fluid treatment medical apparatus of the type having at least a peristaltic pump, comprises:

a rigid casing defining at least a first fluid flow chamber, said casing also having an inlet to said first chamber and an outlet from said first chamber, a first flexible tube having a first and a second end secured to the rigid casing to form a portion of a loop designed to receive a rotor of the medical treatment apparatus peristaltic pump, the first end of the first flexible tube being connected to said first chamber outlet, a second flexible tube having a first end connected to the inlet of said first chamber, a third flexible tube having a first end secured to the rigid casing and in fluid communication with the second end of said first tube, wherein the cassette assembly further comprises:

a rigid tubular piece having:
a first end connector,
a second end connector, opposite said first end connector, and
an intermediate portion extending between said first and second end connectors for subjecting the fluid flowing through said intermediate portion to a measurement of at least a fluid parameter,
the first end connector of the rigid tubular piece being secured to one selected in the group comprising: a second end of the second flexible tube, and a second end of the third flexible tube.

The cassette assembly can comprises one or more of the following features:

said intermediate portion can have a constant cross section.

said intermediate portion can have a toric cross section.

said intermediate portion can be at least partially transparent to electromagnetic and/or acoustic waves.

when the first end connector of the rigid tubular piece is secured to the second end of the second flexible tube, and the second flexible tube can have an axial extension L, an internal diameter Di, an external diameter De and a hardness H satisfying at least one of the following conditions:

$L/Di > 10$ $2L/(De-Di) > 50$ $H < 85$ Shore A to thereby defining a deformable portion between the rigid casing and the rigid tubular piece.

when the first end connector of the rigid tubular piece is secured to the second end of the third flexible tube, and the third flexible tube may have an axial extension L, an internal diameter Di, an external diameter De and a hardness H satisfying at least one of the following conditions:

$L/Di > 10$ $2L/(De-Di) > 50$ $H < 85$ Shore A to thereby defining a deformable portion between the rigid casing and the rigid tubular piece.

said first and second end connectors may have an external prismatic surface and an internal cylindrical surface, the external prismatic surface of at least one of said end connectors bearing a radially protruding element which is designed to cooperate in use with a corresponding mating recess provided on a holder of the medical apparatus; the radially protruding element may be in one piece with the rigid tubular piece and comprises side walls emerging from external surface of the end connector and a terminal wall extending transversally to said side walls; the side walls of the protruding element may be slightly converging when moving apart from the external surface of the end connector, and said terminal wall may be substantially flat and parallel to a longitudinal axis of development of the rigid tubular piece.

said first and second connectors may have an external prismatic surface and an internal prismatic surface, the external prismatic surface of at least one of said connectors bearing a radial recess which is designed to cooperate in use with a corresponding mating protrusion on a holder of the medical apparatus. The external prismatic surface may have a pair of expansions comprising two longitudinal and parallel fins defining the radial recess.

the rigid plastic casing may have front and rear walls spaced from each other and a side wall between said front and rear walls to define said first fluid flow chamber.

the rigid casing may be a one piece body in transparent plastic material and wherein the rigid tubular piece is a one piece body in transparent plastic material.

the first end connector of the rigid tubular piece may be secured to the second end of the second flexible tube, said second end connector of the rigid tubular piece being secured to a first end of a fourth flexible tube; in this case the second end of the fourth flexible tube bears a connector for a vascular access device and the second end of the third tube bears a connector to a blood treatment unit.

the first end connector of the rigid tubular piece may be secured to the second end of the third flexible tube, said second end connector of the rigid tubular piece being secured to a first end of a fourth flexible tube. In this case the second end of the second flexible tube bears a connector for a vascular access device and the second end of the fourth tube bears a connector to a blood treatment unit.

the rigid casing can also comprise an intermediate wall extending between the side walls to define a second fluid flow chamber.

the rigid casing can also include a rigid channel extending above the fluid flow chamber and connecting the first end of the third flexible tube to the second end of said first tube.

the second fluid flow chamber may have a second inlet and a second outlet, said second inlet being secured to an end of a fifth flexible tube having its other end bearing a connector to a blood treatment unit and said second outlet being secured to an end of a sixth flexible tube having its other end bearing a connector to an access device.

A further object of the invention is a medical apparatus adopting a cassette assembly according to the invention.

Another object of the invention is a medical apparatus having the ability to cooperate with the rigid tubular piece of the cassette assembly for carrying our reliable and repeatable detections of the parameter under measure, for instance haemoglobin concentration.

A further object of the invention is a medical apparatus having the ability to improve reliability in the detections by insuring proper positioning of the right rigid tubular piece to be subject to measure, in correspondence of the right position.

According to one embodiment, the medical apparatus is able to generate a consent signal for the haemoglobin concentration measurement to take place only when the proper tubular piece in the proper position is detected.

One or more of the above objects are reached by a cassette assembly according to one of more corresponding aspects of the invention, as delineated in the appended cassette assembly claims.

One or more of the above objects are also reached by a medical apparatus according to one of more corresponding aspects of the invention, as delineated in the appended medical apparatus claims.

According to the invention a medical apparatus for an extracorporeal fluid treatment has:
- a main support structure having at least a receiving portion and a holder,
- a cassette assembly according to anyone of the preceding claims, the cassette assembly being mounted on the receiving portion carried by the main support structure,
- at least a peristaltic pump carried by the main support structure and having a rotor, the portion of loop of the cassette assembly receiving the rotor of the peristaltic pump,
- the holder holding the rigid tubular piece of the cassette assembly.

The apparatus may also include one or more of the following features:
- the holder may comprise a base carried by the support structure and defining a seat for receiving at least the rigid tubular piece, and a first sensor and comprising at least an emitter of a signal and a detector which can detect a return signal.
- the emitter may comprise a waves emitter emitting electromagnetic or acoustic waves with an emission intensity and frequency and the detector may comprise a detector of electromagnetic or acoustic waves which can detect a received intensity and/or frequency.
- a control unit connected to the first sensor and including means for calculating a property of a fluid circulating through the rigid tubular piece based on one selected in the group comprising:
  - said emission and received intensities
  - said emission and received frequencies
  - a phase shift between said emitted and received waves.
- the means for calculating a property of a fluid circulating through the rigid tubular piece may include:
  - means for calculating a difference or a ratio between the emission intensity and the received intensity,
  - means for determining an absorption of energy by the fluid circulating through the rigid tubular piece based on said difference or on said ratio,
  - means for determining the property of the fluid circulating through the rigid tubular piece based on said absorption.
- when the fluid is blood the property of the fluid circulating through the rigid tubular piece includes at least one selected in the group comprising: blood density, blood hematocrit, blood hemoglobin concentration, mean blood cellular volume.
- the emitter and detector may be positioned in correspondence of said intermediate portion of the rigid tubular piece.
- the holder may also comprise a closure element which is coupled to the base and which can be moved between a closed position, where it closes the seat and secures in position the rigid tubular piece, and an open position, where the closure element leaves the seat open thereby allowing insertion or removal of the tubular piece into or from the seat. The emitter and detector may positioned according to one of the configuration selected in the group comprising: a solution where the closure element rigidly carries one of said emitter and detector, the base rigidly carrying the other of said emitter and detector, a solution where the closure element rigidly carries both said emitter and detector, a solution where the base rigidly carries both said emitter and detector.
- the sensor may have a reflector presenting a reflective surface entirely surrounding the intermediate portion, the emitter and detector positioned in correspondence of said reflector.
- the closure element may include a door hinged around a pivot axis on one side of the base, the door turning around said pivot axis when moving between said open and close positions, the door comprising at least one lock member cooperating with a counter-lock member on the base, the lock and counter-lock member being coupled in correspondence of said closed position. The door may have two lock members, one on each side cooperating with one respective counter-lock member on the base, the lock and counter-lock members being coupled in correspondence of said closed position. Each lock member may comprise an elastically deformable flat wing having one end secured to the door and one end carrying a protrusion, in correspondence of said closed position the protrusion engaging a correspondingly shaped recess defined on the base.
- the holder may also comprise a second sensor which is at least capable of detecting when the closure element is in its closed position and of emitting a corresponding closure signal.
- the control unit may be connected to the second sensor and comprise means for determining whether or not the closure element is in its closure position based on said closure signal emitted by the second sensor.
- the seat may comprise a first portion counter-shaped to first end connector and a second portion counter-shaped to the second end connector.
- the first and second portions of the seat may present a prismatic surface, the prismatic surface of at least one of said first and second portions bearing a radial recess which cooperates with the corresponding mating protrusion present on one of the end connectors.
- the first and second portions of the seat may present a prismatic surface, the prismatic surface of at least one of said first and second portions bearing a radial protrusion which cooperates with the corresponding mating recess on one of the end connectors.
- a third sensor may be associated to one of said first and second portions of the seat to detect the presence and proper position of the rigid tubular piece in the holder seat and emit a corresponding matching signal.
- depending upon the case the third sensor may be constructed to detect presence of a matching coupling between the protrusion on the end connector and the radial recess on the seat and to emit a corresponding matching signal or to detect presence of a matching coupling between protrusion on the seat and radial recess on the end connector and to emit a corresponding matching signal.
- the control unit may be connected to the third sensor and include means determining whether the proper rigid tubular piece is in the right position within the seat based on said matching signal emitted by the third sensor.
- a treatment unit may be associated to the main support structure, the treatment unit having a semipermeable membrane dividing the treatment unit in at least a first chamber for the flow of blood which is in fluid communication with the cassette assembly and in a second chamber which has at least an outlet port in fluid communication with an outlet line, and there may be provision for means for regulating the net flow of plasma water passing through the semipermeable membrane from the first to the second chamber and viceversa. Means may be present for controlling the regulating means based on values taken by said calculated property.

The control unit may include means for determining whether the proper rigid tubular piece is in the right position within the seat based on said matching signal emitted by the third sensor. The control unit comprises means for commanding the means for activating the first sensor only when the means for determining have positively concluded that the proper rigid tubular piece is in the right position within the seat.

The control unit may also comprise means for signaling that the fluid property cannot be calculated when the means for determining have not positively concluded that the proper rigid tubular piece is in the right position within the seat.

The control unit may also comprise means for activating said means for controlling the regulating means only when the means for determining have positively concluded that the proper rigid tubular piece is in the right position within the seat.

When the apparatus comprises a supply line for a treatment liquid connected at an inlet of the second chamber of the blood treatment unit, then means for regulating a chemical composition of the treatment liquid in the supply line may be present, and the control unit may also comprise means controlling the means for regulating the chemical composition based on values taken by said calculated property.

Finally the invention concerns a rigid tubular piece for an extracorporeal blood circuit, the rigid tubular piece having:
a first end connector,
a second end connector, opposite said first end connector, and
an intermediate portion extending between said first and second end connectors for subjecting the fluid flowing through said intermediate portion to a measurement of at least a fluid parameter.

Further possible features of the rigid tubular piece and of a cassette assembly rigidly bearing the rigid tubular piece are described in the claims.

SHORT DESCRIPTION OF THE DRAWINGS

Further features and advantages will be best understood from the detailed description of some non limiting embodiments of the present invention. This description will be carried out hereinafter with reference to the accompanying drawings, also given by way of non-limiting example, in which:

FIG. 11 is an interrupted perspective view of a medical apparatus which can receive the cassette assembly of FIG. 1.

FIG. 20 is a schematic diagram of a blood treatment machine.

DETAILED DESCRIPTION

Figure 1:
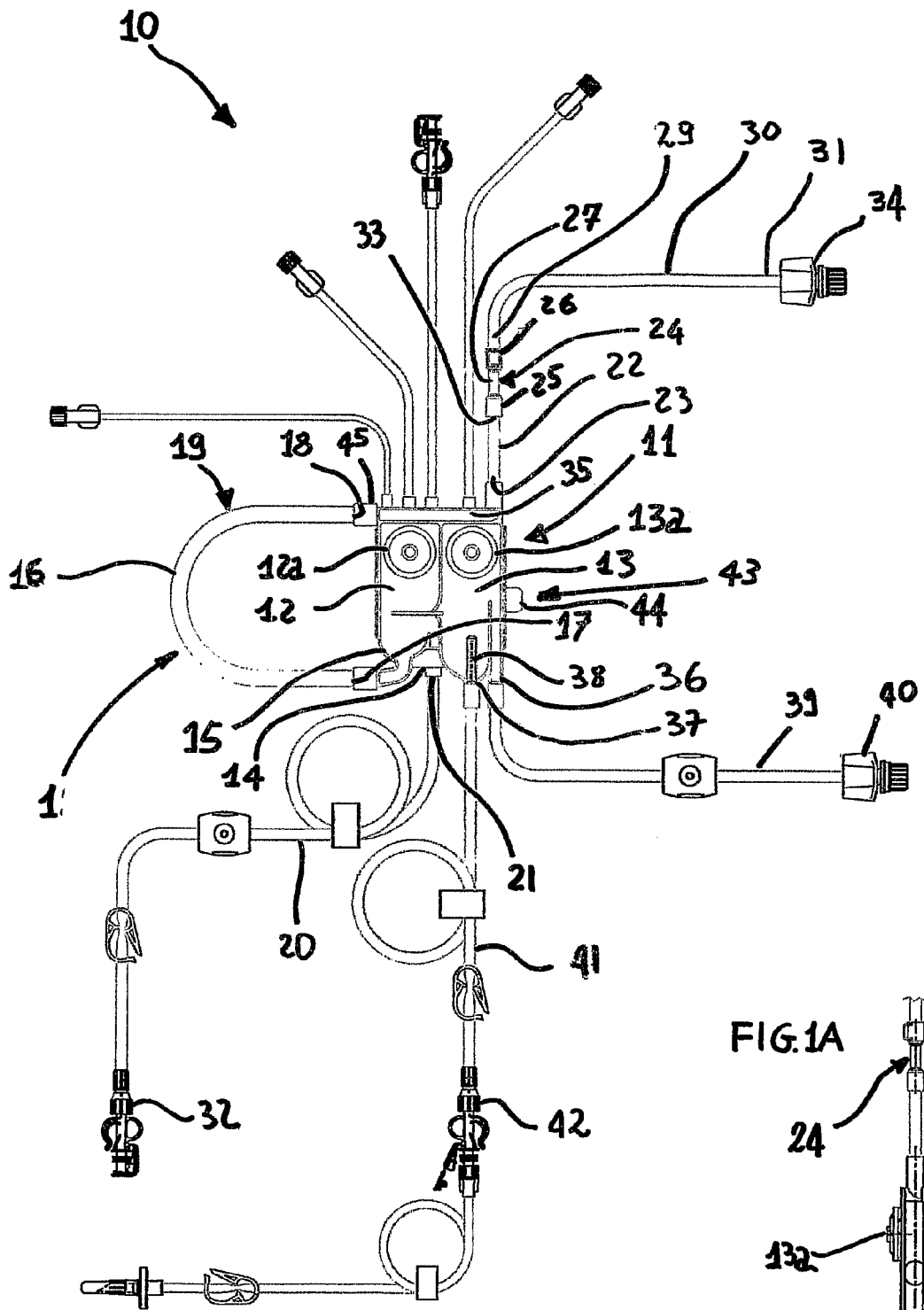
FIG. 1 is an elevation of a first embodiment of a cassette assembly for use with a fluid treatment medical apparatus.
Figure 1A:
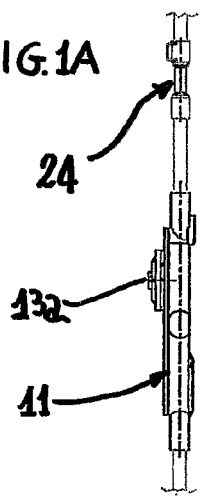
FIG. 1A is a side view of a portion of the embodiment of FIG. 1.

With reference to the enclosed drawings, reference number 1 denotes a medical apparatus for an extracorporeal fluid treatment. In particular the apparatus can be an apparatus for the treatment of blood, such as by way of non-limiting example a machine for the treatment of renal or liver insufficiency. In the example shown in the attached figures, the medical apparatus 1 is a machine for one or more of the following extracorporeal blood treatments: hemodialysis, hemofiltration, ultrafiltration, hemodiafiltration, and plasmaphaeresis.

The apparatus 1 comprises a main support structure 2 and operating panel 3, which can be in a front position of the apparatus, including a user interface 4 (only schematically represented), one or more pumps 5 (volumetric pumps of the type acting in deformation of deformable tube portions, such as peristaltic pumps), and at least a holder 6 so constructed as to receive a rigid tubular piece to be subject to a non invasive measurement as it will be explained in detail herein below.

The apparatus also presents an auxiliary holder 7 for receiving at least a blood treatment unit 8 (for instance a dialyzer or an ultrafilter or an hemofilter or an hemodiafilter or a plasmafilter). The blood treatment unit can comprise, in a manner per se known and therefore not further detailed, a first and a second compartment separated by a semipermeable membrane. The first compartment is for the passage of blood and the second compartment is for the passage of discarded substances and/or treatment liquid.

The medical apparatus has also a receiving portion 9 for holding a cassette assembly 10. In the enclosed figures the receiving portion is on the front panel 3 in close proximity of the peristaltic pump 5 and cooperates with a pivoting door which serves to secure in position the cassette assembly and the portion of tubing cooperating with the rotor.

The disposable cassette assembly 10 comprises a rigid casing 11 defining at least a first fluid flow chamber 12; in reality in the embodiment shown the rigid casing defines two chambers 12, 13. For instance, in order to define a two chambers rigid structure, the rigid casing can have front and rear walls spaced from each other and side walls between said front and rear walls as well as an intermediate wall which cooperates with the side walls to define said two chambers.

Pressure transducers 12a and 13a can be associated to each one of the two chambers walls, in a manner per se known and not further detailed.

When there is the need to see the material flowing inside the cassette assembly, as it is desirable in case of blood treatments, then rigid casing can be in transparent plastic material.

The rigid casing, for instance made in one piece transparent PVC material, also defines an inlet 14 to the first chamber 12 and an outlet 15 from said first chamber. In the embodiment of FIG. 1 both the inlet 14 and the outlet 15 are placed in correspondence of an inferior portion of the rigid casing 11.

Figures 2, 2A:
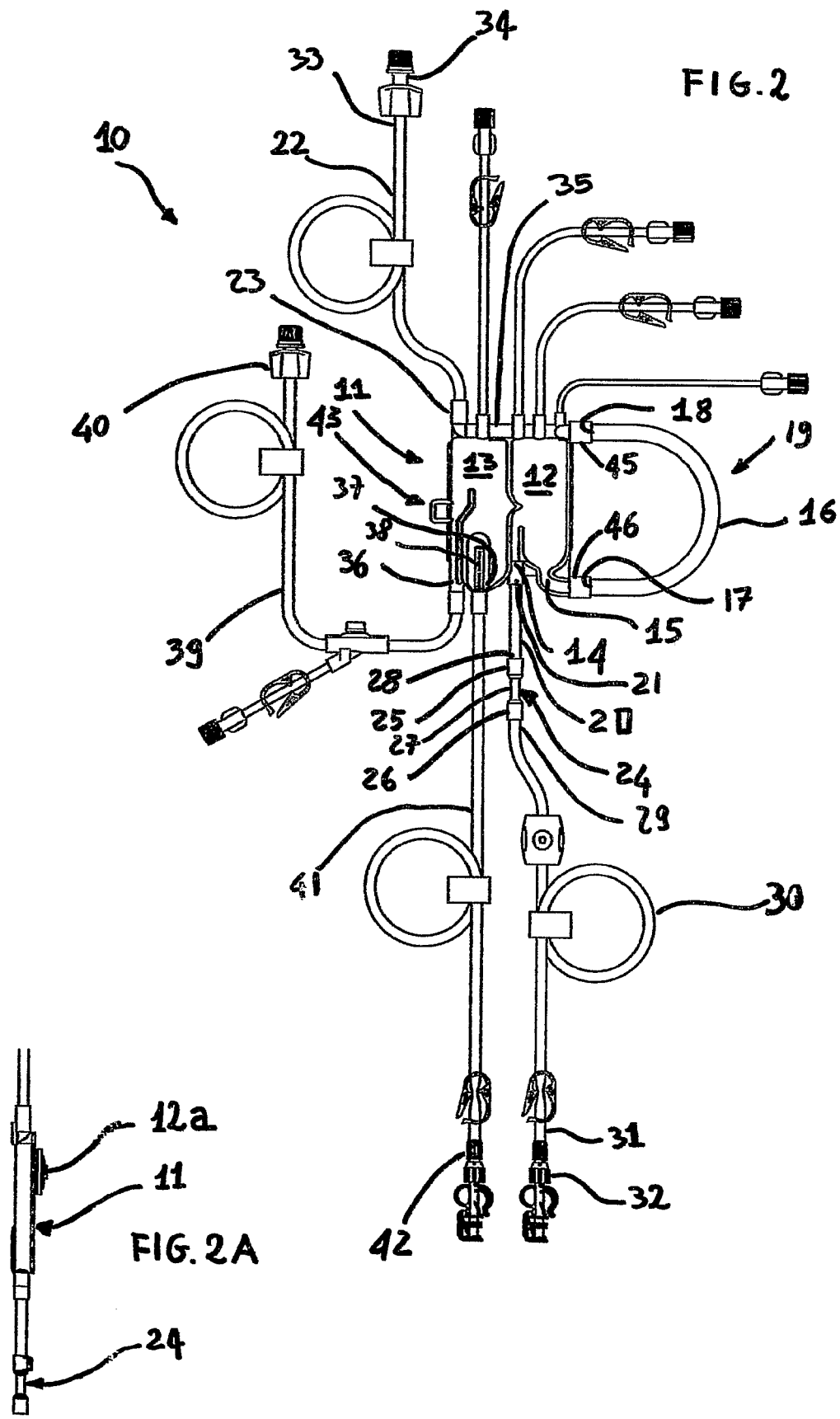
FIG. 2 is an elevation of a second embodiment of cassette assembly for use with a fluid treatment medical apparatus.
FIG. 2A is a side view of a portion of the embodiment of FIG. 2.
Figure 3:
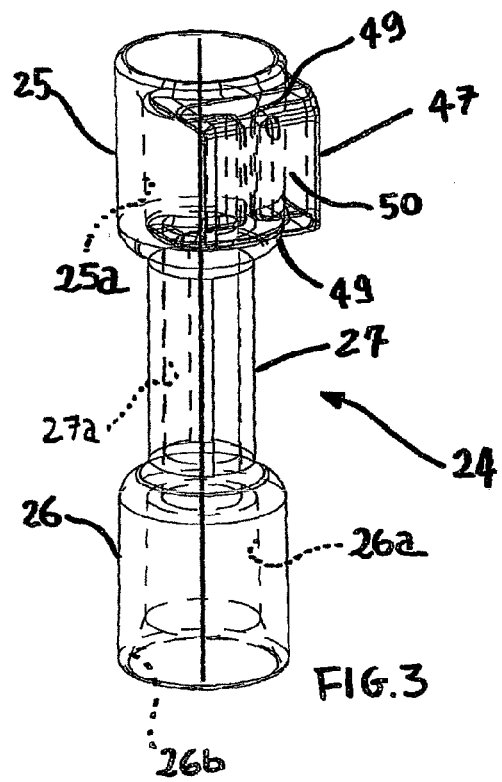
FIG. 3 is an enlarged perspective view of a rigid tubular piece for use in the cassette assembly of FIG. 1 or FIG. 2.
Figure 8:
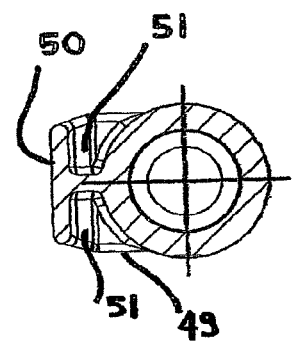
FIG. 8 is a section view along section plane VIII-VIII of FIG. 4.
Figure 10:
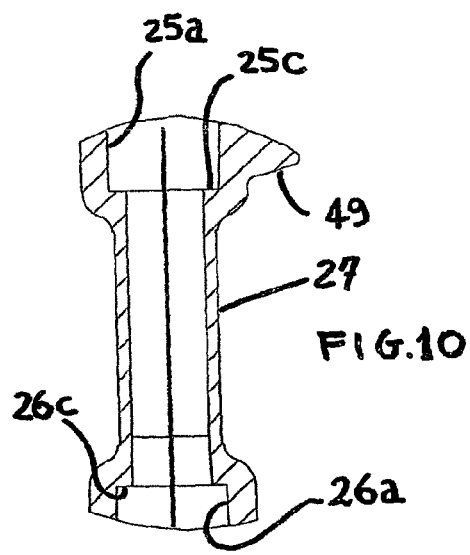
FIG. 10 is an enlarged view of a portion of the section view of FIG. 6.
Figure 5:
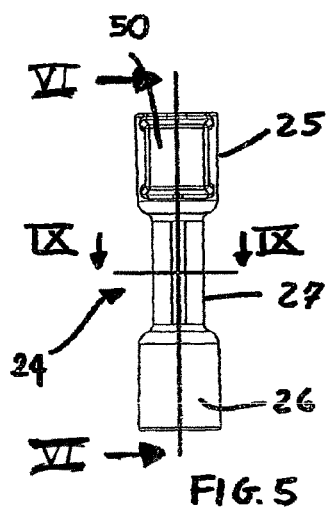
FIG. 5 is a side view of the rigid tubular piece of FIG. 3.
Figure 6:
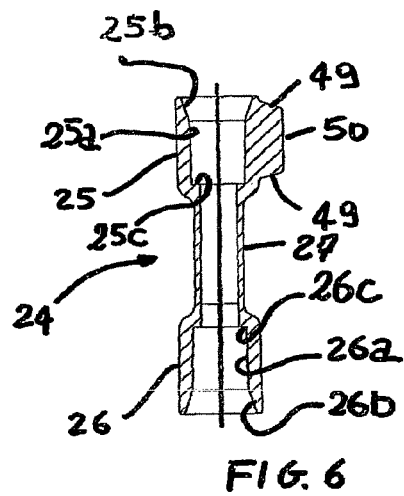
FIG. 6 is a section view along section plane VI-VI of FIG. 5.
Figure 7:
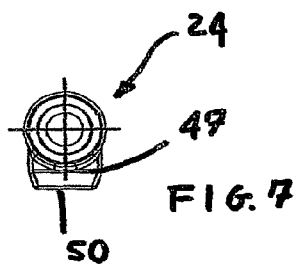
FIG. 7 is a plan view of the rigid tubular piece of FIG. 5.
Figure 4:
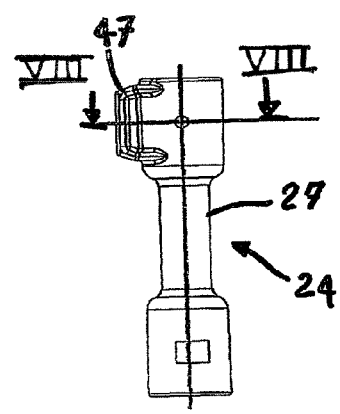
FIG. 4 is a front view of the rigid tubular piece of FIG. 3.
Figure 9:
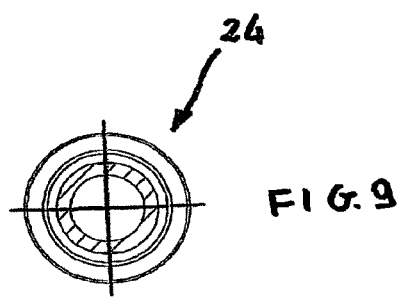
FIG. 9 is a section view along section plane IX-IX of FIG. 5.

The cassette assembly comprises a plurality of flexible tubes engaged to the rigid casing. More in detail, a first flexible tube 16 has a first and a second end 17 and 18 secured to the rigid casing to form a portion of a loop 19 designed to receive the rotor of peristaltic pump 5: the first end 17 of the first flexible tube is connected to said first chamber outlet 15 while the second end 18 of the first flexible tube is secured to the casing in a position which is vertically displaced with respect to the first end, as shown in FIGS. 1 and 2.

A second flexible tube 20 has a first end 21 connected to the inlet 14 of said first chamber 12. A third flexible tube 22 has a first end 23 secured to the rigid casing 11 and in fluid communication with the second end 18 of said first tube 16.

The cassette assembly 10 further comprises a rigid tubular piece 24 having a first end connector 25, a second end connector 26 opposite said first end connector 25, and an intermediate portion 27 extending between said first and second end connectors 25, 26. The intermediate portion 27 is designed and calibrated because in use, when it is flown through by blood or other fluid, it is adopted for subjecting the fluid flowing through said intermediate portion 27 to non-invasive measurement of certain parameters of the fluid. The intermediate portion 27 may have a constant cross section and may be made of at least partially transparent material.

Of course the cross section could also be variable but this may entail a more complex measurement procedure. In term of shape, again referring to the embodiment shown, the intermediate portion 27 can have a toric cross section.

In the embodiment shown the rigid tubular piece 24 is in a single piece made in transparent plastic material, for instance PVC (of course other rigid plastic materials can alternatively be used).

In the embodiment of FIG. 2 the first end connector 25 of the rigid tubular piece 24 is secured to the second end 28 of the second flexible tube 20. In this case, the second flexible tube 20 has a prefixed axial extension sufficient to absorb, by axial deformation or by bending, all relative displacements between the rigid casing 11 and the rigid tubular piece 24 when, in use, they are in mounted on the medical apparatus 1.

For instance, the second flexible tube 20 can be equal to or longer than the axial length of the rigid tubular piece 24. According to another aspect, the axial length of the second flexible tube 20 of FIG. 2 can be greater than three times its external diameter.

In accordance with a further, alternative or additional, aspect the second flexible tube has an axial extension L, an internal diameter Di, an external diameter De and a hardness H satisfying at least one of the following conditions:

$L/Di > 10$ $2L/(De-Di) > 50$ $H < 85$ Shore A to thereby defining a deformable portion between the rigid casing and the rigid tubular piece thereby isolating the holder from vibrations which may deteriorate quality of the measurements of said property.

In the example shown:

$L/Di > 18$ $2L/(De-Di) > 55$ $H < 80$ Shore A

In the case of FIG. 2 the second end connector 26 of the rigid tubular piece 24 is secured to a first end 29 of a fourth flexible tube 30, while the second end 31 of the fourth flexible tube 30 bears a connector 32 for a vascular access device (such as a cannula, a needle, a catheter, or other access) and the second end 33 of the third tube 22 bears a connector 34 for coupling to a corresponding counter connector on the inlet port of the blood treatment unit first chamber (not shown).

In the embodiment of FIG. 1 the first end connector 25 of the rigid tubular piece 24 is secured to the second end 33 of the third flexible tube 22. In this case, the third flexible tube 22 has a prefixed axial extension which is sufficient to absorb, by axial deformation or by bending, all relative displacements between the rigid casing 11 and the rigid tubular piece 24 when, in use, they are in mounted on the medical apparatus 1.

For instance, the third flexible tube 22 can be equal to or longer than the axial length of the rigid tubular piece 24.

According to another aspect, the third flexible tube has an axial extension L, an internal diameter Di, an external diameter De and a hardness H satisfying at least one of the following conditions:

$L/Di > 10$ $2L/(De-Di) > 50$ $H < 85$ Shore A to thereby defining a deformable portion between the rigid casing and the rigid tubular piece which is able to absorb any relative movement between the rigid casing and the holder, thereby isolating the holder from vibrations which may deteriorate quality of the measurements of said property.

In the example shown:

$L/Di > 18$ $2L/(De-Di) > 55$ $H < 80$ Shore A

In the case of FIG. 1 the second end connector 26 of the rigid tubular piece 24 is secured to a first end 29 of a fourth flexible tube 30 and the second end 31 of the fourth tube 30 bears a connector 34 to corresponding counter connector on the inlet port of the blood treatment unit first chamber (not shown). In the example of FIG. 1 the second flexible tube 20 bears at a second end thereof a connector 32 for a vascular access device (such as a cannula, a needle, a catheter, or other access).

In both the embodiments of FIGS. 1 and 2 the cassette assembly 10 includes a rigid channel 35 extending above the fluid flow chambers 12, 13 and connecting the first end 23 of the third flexible tube 22 to the second end 18 of said first tube 16. Moreover the second fluid flow chamber 13 has a second inlet 36 and a second outlet 37 (where a venous filter 38 can operate): the second inlet 36 is secured to an end of a fifth flexible tube 39 having its other end bearing a connector 40 to a blood treatment unit for coupling to a corresponding counter connector on the outlet port of the blood treatment unit first chamber (not shown). The second outlet 37 of the second chamber 13 is secured to an end of a sixth flexible tube 41 having its other end bearing a connector 42 to an access device (such as a cannula, a needle, a catheter, or other access).

In the embodiments shown mounting means 43 is associated to the cassette assembly for mounting said casing on said machine. In this case the mounting means comprises at least one projection 44 rigidly carried by the rigid casing. The mounting means 43 also include tubular extensions 45, 46 rigidly carried on one side of the rigid casing 11 and secured to a respective opposite end of said first flexible tube 16. This mounting means 43 cooperates with corresponding pick-up elements on the front panel of the machine in correspondence of said receiving portion. Of course other mounting means could be provided for, such as extensions or recesses in positions different from those above described, or an appropriate shaping of the cassette assembly walls and corresponding receiving portion and so on.

Going now into a more detailed description of the rigid tubular piece 24 (see FIGS. 3 to 9, 14, 15), the first and second end connectors 25, 26 have an external prismatic, for instance cylindrical, surface and an internal prismatic surface; the internal prismatic surface of each end connector in the embodiments shown presents a main cylindrical tract 25a, 26a and a frustum-conical leading edge 25b, 26b. The cylindrical tracts have a diameter grater than that of the intermediate portion inner surface 27a in order to define an abutment 25c, 26c for the connection of the tube end portions. Notice that the intermediate portion 27 internal surface 27a can be prismatic, and in this case is cylindrical, and extends in immediate prosecution of the abutment. In practice in order to avoid stagnation areas, the diameter of the cylindrical tracts 25a, 26a can be made equal to that of the intermediate portion inner surface 27a plus two times the thickness of the end portions of the tube secured in correspondence of said end connectors. This assures that in use a continuous and smooth channel is created through the whole rigid tubular piece.

The external prismatic surface of at least one of said end connectors bears a radially protruding element 47 which is designed to cooperate in use with a corresponding mating recess 48 provided on the holder 6 of the medical apparatus.

The radially protruding element 47 is in one piece with the rigid tubular piece 24 and comprises side walls 49 emerging from external surface of one of the end connectors and a terminal wall 50 extending transversally to side walls 49. In the embodiment shown two opposite side walls 49 can protrude from the surface of the end connector and terminate into the terminal wall 50. The protrusion can also present two opposite side indents 51, which in the example of FIGS. 3-10 extend inside the protrusion conferring to the protrusion a cross section in the shape of a T (see FIG. 8).

The opposite side walls of the protruding element can be slightly converging (see FIGS. 6 and 10), at least in correspondence of a terminal portion thereof, when moving apart from the external surface of the end connector; the terminal wall is substantially flat and parallel to a longitudinal axis of development of the rigid tubular piece.

Alternatively or in combination with the protrusion (please refer to the example of FIGS. 14-17, one of the end connectors 25, 26 can present one or more recesses 52 on an external surface thereof. In particular, referring to the embodiment shown, the first and second connectors which have an external prismatic surface and an internal cylindrical surface can bear a pair of expansions 53 defining a radial recess 52 which is designed to cooperate in use with a corresponding mating protrusion 54 on the holder of the medical apparatus. In the embodiment shown, the expansions comprise two longitudinal and parallel fins providing a radial recess with a substantially U-shaped cross section. When the protrusion mates with the recess 52, the expansions 53 engage counter-shaped cavities 55 on the holder 6

Going now back to the overall apparatus, apparatus 1 of the enclosed figures comprises, as mentioned, the holder 6 for the rigid tubular piece 24. This holder may include a base 56 carried by the support structure and defining a seat 57 for receiving at least the rigid tubular piece 24, and a first sensor 58 associated to the base and comprising at least an emitter of a signal and a detector which can detect a return signal. The rigid tubular piece comprises at least a portion which is transparent or at least partially transparent to said signals in order to allow a non invasive measurement made taking into account the influence of the fluid on said signals.

In greater detail, the emitter comprises a waves emitter emitting electromagnetic or acoustic waves with specified emission property (e.g. specified intensity or frequency) and the detector comprises a detector of electromagnetic or acoustic waves which can detect a received intensity or frequency or phase.

A control unit 61 connected to the first sensor includes means for calculating a property of a fluid circulating through the rigid tubular piece based on said emission and received intensities or on the phase shift between the emitted and received signals or on alteration of the frequency between emitted and received signal.

In the embodiment now described, the means for calculating a property of a fluid circulating through the rigid tubular piece can include:

means for calculating a difference or a ratio between the emission intensity and the received intensity, means for determining an absorption of energy by the fluid circulating through the rigid tubular piece based on said difference or on said ratio, means for determining the property of the fluid circulating through the rigid tubular piece based on said absorption.

When the fluid is blood, the property of the fluid circulating through the rigid tubular piece includes at least one selected in the group comprising:

blood density,
blood hematocrit,
blood hemoglobin concentration,
mean blood cellular volume.

The emitter and detector and are positioned in correspondence of said intermediate portion, which is at least in part transparent to said acoustic or electromagnetic waves, of the rigid tubular piece.

The holder also comprises a closure element 62 which is coupled to the base and which can be moved between a closed position, where it closes the seat and secures in position the rigid tubular piece, and an open position, where the closure element leaves the seat open thereby allowing insertion or removal of the tubular piece into or from the seat. The closure element 62 rigidly can carry one of said emitter and detector, while the base rigidly carries the other of said emitter and detector. Alternatively both emitter and detector can be on the base or both on the closure element. When the closure element is closed onto the base, the emitter and detector act in direct contact to the intermediate portion external surface.

In the embodiment shown, the closure element includes a door hinged around a pivot axis 63 on one side of the base, so that the door can turn around said pivot axis when moving between the open and close positions.

Figure 12:
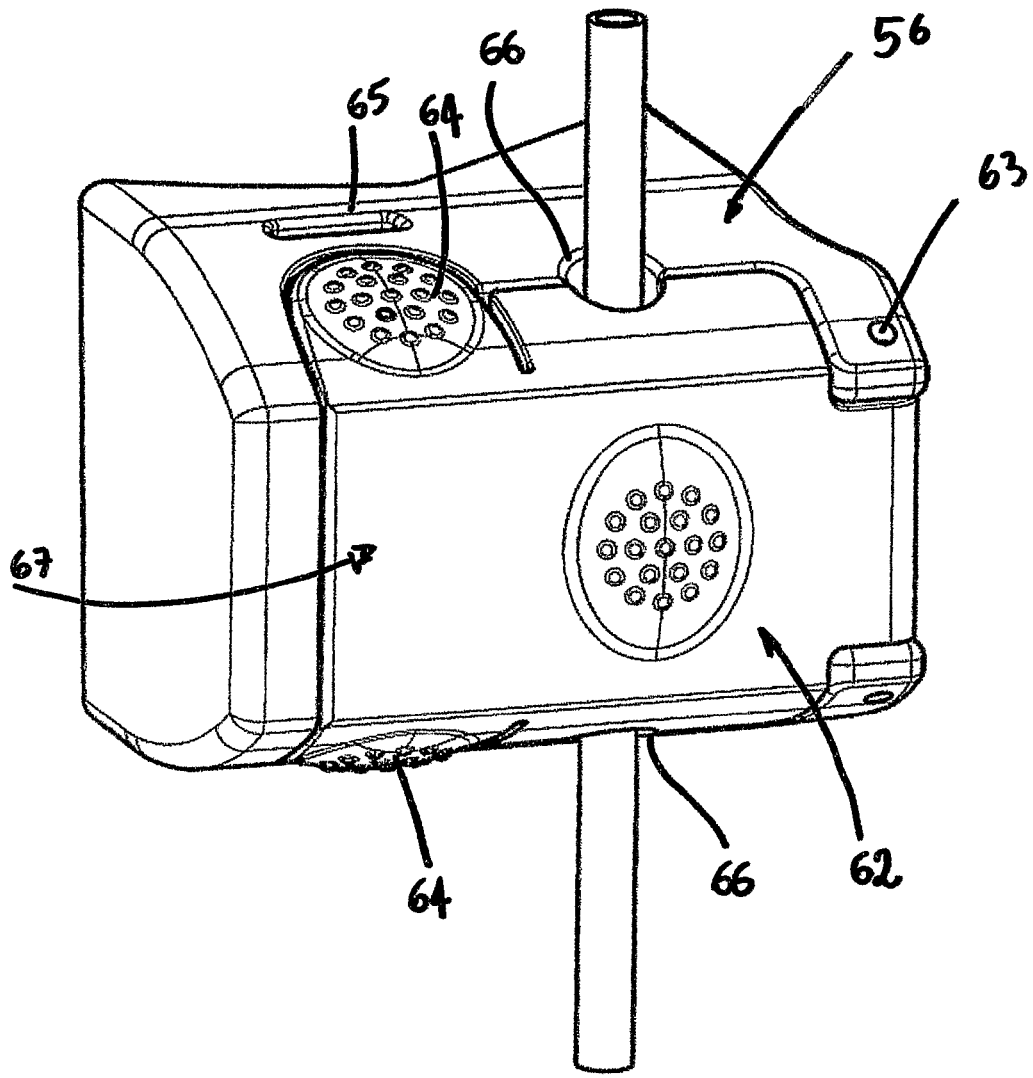
FIG. 12 is a perspective view concerning an holder of the apparatus of FIG. 11, in closed position.
Figure 13:
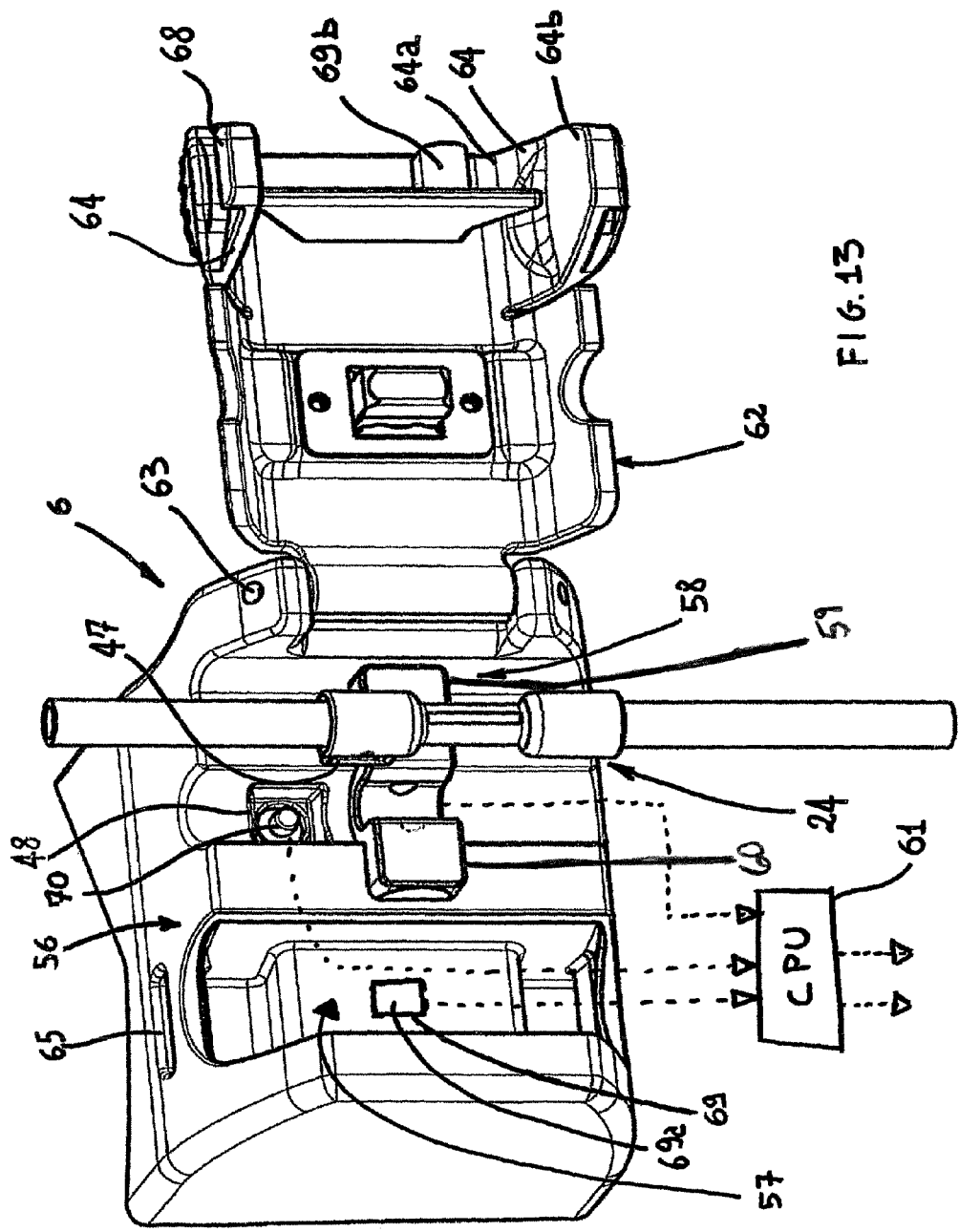
FIG. 13 is a perspective view concerning an holder of the apparatus of FIG. 11, in open position.
Figure 16:
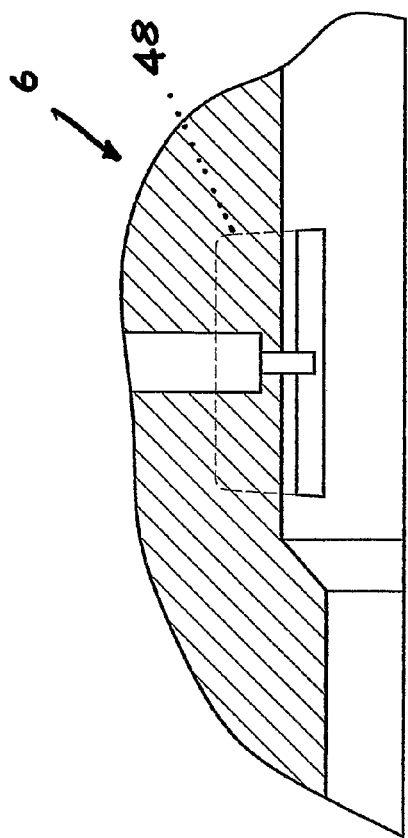
FIGS. 16 and 17 show a cross and longitudinal section of the seat where the rigid tubular piece of FIG. 14 can operate.
Figure 17:
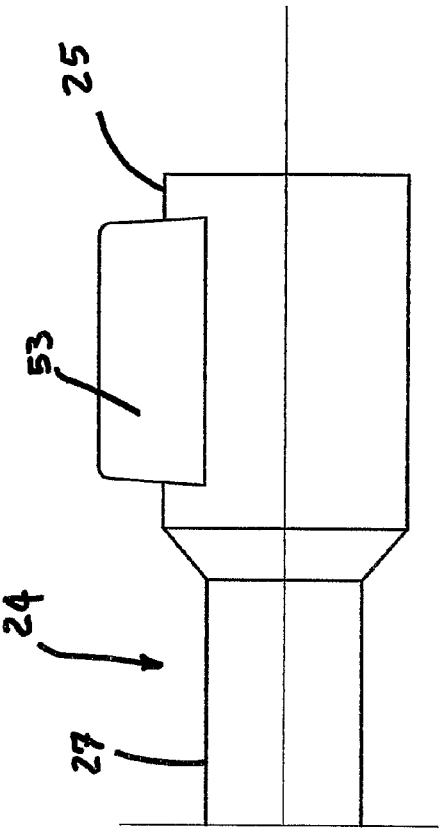
Figure 14:
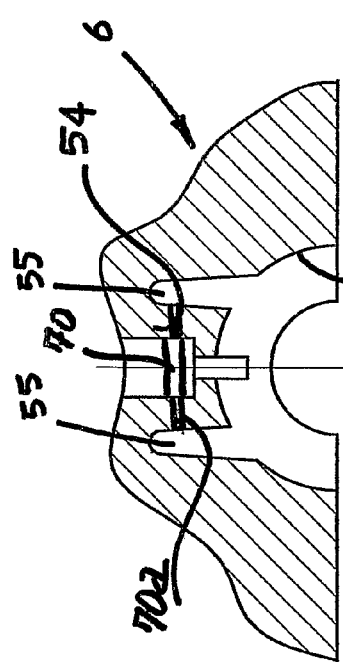
FIG. 14 shows an enlarged plan view of an alternative embodiment of the rigid tubular piece associated with the cassette assembly of FIGS. 1 and 2.
Figure 15:
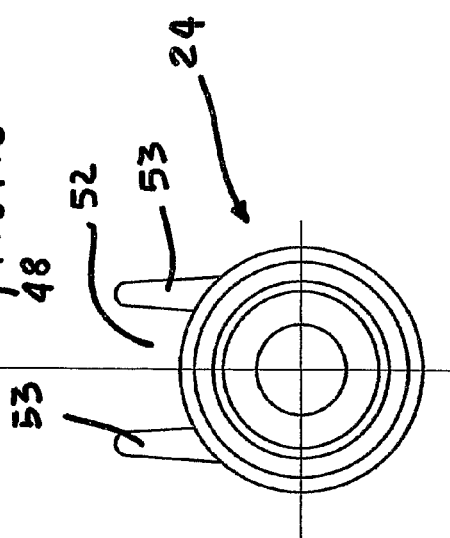
FIG. 15 shows an enlarged and interrupted side view of the rigid tubular piece of FIG. 14.

The door comprises at least one lock member 64 cooperating with a counter-lock member 65 on the base 56. When the door is in the closed position, the lock and counter-lock member are coupled the one with the other as shown in FIG. 12, leaving two openings 66 for the passage of the tube ends connected with the rigid tubular piece 24.

In the example, two lock members 64, one on each side are cooperating with respective counter-lock members on each side of the base and extend in an area 67 of the holder opposite to the pivot axis so that when closing the door the rigid tube portion and its seat in the holder extends between the pivot axis and the door lock and counter-lock members.

Each lock member can comprise an elastically deformable flat wing having one end 64a secured to the door and one end 64b carrying a protrusion 68 designed for engaging a correspondingly shaped counter-lock member 65 in the form of a recess (in the embodiment a through slit) defined on the base.

The holder 6 also comprises a second sensor 69 which is at least capable of detecting when the closure element is in its closed position and of emitting a corresponding closure signal. Of course the sensor 69 could be more sophisticated and be able to monitor each position of the closure element. In the embodiment shown the sensor is a hall sensor 69a housed on the base 56 and cooperating with a magnet 69b on the door. Of course one could use alternative solutions, such as a switch or a relays or other equivalent solutions able to detect closure of the door 62. The control unit is also connected to the second sensor and comprises means for determining whether or not the closure element is in its closure position based on said closure signal emitted by the second sensor.

The holder can also present a third sensor 70 operatively associated to one of said first and second portions of the seat to detect the presence and proper position of the rigid tubular piece in the holder seat and emit a corresponding matching signal. More in detail the third sensor can be associated to one of said first and second portions in correspondence or in close proximity of said radial recess 48 (or radial protrusion 54 as the case may be) of the seat. The third sensor is constructed to detect presence of a matching coupling between the protrusion 47 on the end connector and the radial recess on the seat and to emit a corresponding matching signal.

Alternatively if the embodiment of FIGS. 14-17 the third sensor is operatively associated to one of said first and second portions in correspondence of the radial protrusion of the seat and is constructed to detect presence of a matching coupling between protrusion 54 on the seat and radial recess 52 on the end connector and to emit a corresponding matching signal. In reality in the embodiment of FIG. 16 the sensor 70 is placed on the protrusion and detects presence of the fins 53 in the cavities 55. Channels 70a may be provided to send an optical information when fins 53 occupy the cavities 55.

Figure 19:
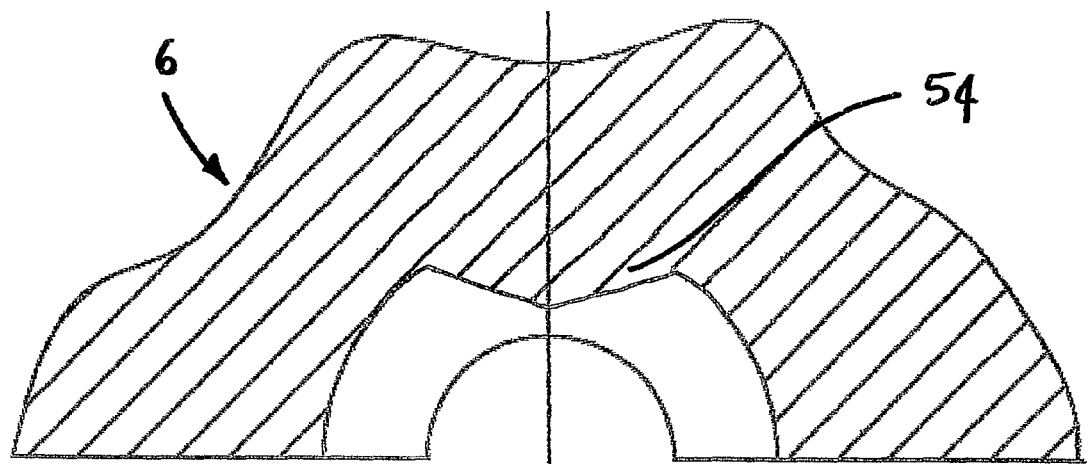
FIGS. 18 and 19 show in interrupted cross sectional view an alternative shape for the seat and the rigid tubular piece.
Figure 18:
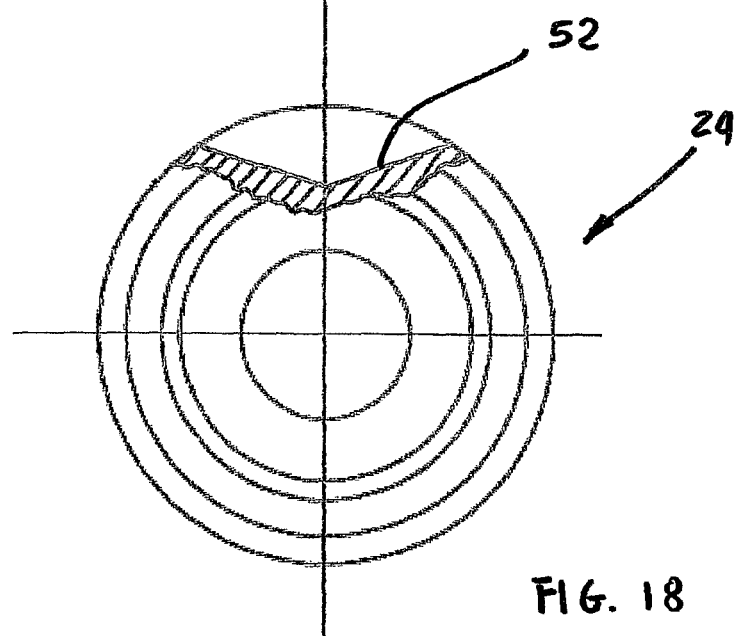

The further alternative of FIGS. 18 and 19 shows an alternative shape for the protrusion on the seat of holder 6 and the recess 52 on the end connector or connectors.

In any case the control unit connected to the third sensor includes means for determining whether the proper rigid tubular piece is in the right position within the seat based on said matching signal emitted by the third sensor.

As mentioned a treatment unit 8 is associated to the main support structure, the treatment unit having a semipermeable membrane 8a dividing the treatment unit in at least a first chamber 71 for the flow of blood which is in fluid communication with the cassette assembly 9 and in a second chamber 72 which has at least an outlet port in fluid communication with an outlet line 73

The apparatus may include means for regulating 74 the net flow of plasma water passing through the semipermeable membrane from the first to the second chamber and viceversa. The means 74 are only schematically shown in FIG. 20 as their structure is not relevant (they could include an ultrafiltration pump or two pumps one on the fresh treatment liquid inlet line 75 and one on the outlet line 73 which when driven at different speed determine ultrafiltration or backfiltration into the blood circuit 76, or even blood pumps in the blood circuit which can be driven at different speed).

Moreover the apparatus may have means 76 for regulating a chemical composition of the treatment liquid in the supply line (also in this case details are not given because the specific structure is not relevant; by way of example the means 77 may comprise one or more concentrates in liquid and or powder state connected to the line 75 and respective flow regulators such as valves or pumps which are controlled by the control unit to reach the desired composition of the treatment liquid).

The control unit 61 also comprises means controlling the means 77 for regulating the chemical composition based on values taken by said calculated property.

More in detail the control unit may have one or more of the following means:
a) means for determining whether the proper rigid tubular piece is in the right position within the seat based on said matching signal emitted by the third sensor,
b) means for activating said first sensor to emit said signal and detect said return signal,
c) means for calculating a property of a fluid circulating through the rigid tubular piece based on said emission and return signals,
d) means for controlling the regulating means 74 based on values taken by said calculated property,
e) means for controlling the means for regulating the chemical composition 77 based on values taken by said calculated property.

The control unit comprises timing means for sequentially activating the above means a) to e).

The control unit may also comprise the further following means.

According to one aspect of the invention the control unit has means for commanding the activating means only when the means for determining have positively concluded that the proper rigid tubular piece is in the right position within the seat.

According to a further aspect of the invention the control unit also has means for signaling that the fluid property cannot be calculated when the means for determining have not positively concluded that the proper rigid tubular piece is in the right position within the seat.

According to another aspect of the invention the control unit has means for activating said means for controlling the regulating means only when the means for determining have positively concluded that the proper rigid tubular piece is in the right position within the seat.

According to another aspect of the invention the control unit has means for activating said means for regulating a chemical composition of the treatment liquid in the supply line only when the means for determining have positively concluded that the proper rigid tubular piece is in the right position within the seat.

Depending upon the case, the control unit can be an entirely digital unit comprising one or more CPUs, or an analogical control unit, or a combination of the two types just mentioned.

When the control unit is of the analogical type, each of the above listed means of the control unit is defined by a corresponding analogical circuitry in the control unit suitably designed for carrying out the specified function.

When, on the other hand, the control unit is in part or totally of the digital type, then each of the above listed means of the control unit is defined by the CPU when running an appropriate software program or software routine which makes the CPU programmed to define one or more of the above listed control unit means.

The invention claimed is:

1. A medical apparatus for an extracorporeal fluid treatment comprising:
   a main support structure having at least a receiving portion and a holder,
   a cassette assembly comprising:
      a rigid casing defining at least a first fluid flow chamber, said casing also having an inlet to said first chamber and an outlet from said first chamber,
      a first flexible tube having a first and a second end secured to the rigid casing to form a portion of a loop, the first end of the first flexible tube being connected to said first chamber outlet,
      a second flexible tube having a first end connected to the inlet of said first chamber,
      a third flexible tube having a first end secured to the rigid casing and in fluid communication with the second end of said first tube, characterized in that the cassette assembly further comprises:
      a rigid tubular piece having:
   a first end connector,
   a second end connector, and
   an intermediate portion extending between said first and second end connectors for subjecting a fluid flowing through said intermediate portion to a measurement of at least a fluid parameter, the first end connector of the rigid tubular piece being secured to one selected in the group comprising: a second end of the second flexible tube, and a second end of the third flexible tube, the cassette assembly being mounted on the receiving portion carried by the main support structure,
   at least a peristaltic pump carried by the main support structure and having a rotor, the portion of the loop of the cassette assembly receiving the rotor of the peristaltic pump, the holder holding the rigid tubular piece of the cassette assembly, said holder comprising:
   a base carried by the support structure and defining a seat for receiving at least the rigid tubular piece, and
   a first sensor and comprising at least an emitter of a signal and a detector which can detect a return signal,
   wherein the emitter and the detector are positioned in correspondence of said intermediate portion of the rigid tubular piece, and wherein the emitter and the detector are positioned according to one of the configurations selected from the group comprising:
      a configuration in which a closure element rigidly carries one of said emitter and detector, the base rigidly carrying the other of said emitter and detector,
      a configuration in which a closure element rigidly carries both said emitter and detector, or
      a configuration in which the base rigidly carries both said emitter and detector.

2. The apparatus according to claim 1, wherein the emitter comprises a waves emitter emitting electromagnetic or acoustic waves with an emission intensity and frequency and the detector comprises a detector of electromagnetic or acoustic waves for detecting a received intensity and/or frequency, the apparatus comprising a control unit connected to the first sensor and including a module for calculating a property of a fluid circulating through the rigid tubular piece based on one selected in the group comprising:
   said emission and received intensities
   said emission and received frequencies
   a phase shift between said emitted and received waves.

3. The apparatus according to claim 2, wherein the module for calculating a property of a fluid circulating through the rigid tubular piece includes:
   a sub-module for calculating a difference or a ratio between the emission intensity and the received intensity,
   a sub-module for determining an absorption of energy by the fluid circulating through the rigid tubular piece based on said difference or on said ratio,
   a sub-module for determining the property of the fluid circulating through the rigid tubular piece based on said absorption and wherein the fluid is blood and the property of the fluid circulating through the rigid tubular piece includes at least one selected in the group comprising:
   blood density,
   blood hematocrit,
   blood hemoglobin concentration,
   mean blood cellular volume.

4. The apparatus according to claim 2, wherein the holder also comprises the closure element which is coupled to the base and which is movable between a closed position, where the closure element closes the seat and secures in position the rigid tubular piece, and an open position, where the closure element leaves the seat open thereby allowing insertion or removal of the tubular piece into or from the seat, the closure element including a door hinged around a pivot axis on one side of the base, the door turning around said pivot axis when moving between said open and close positions, the door comprising at least one lock member cooperating with a counter-lock member on the base, the lock and the counter-lock member being coupled in correspondence of said closed position, the door comprises two lock members, one on each side cooperating with one respective counter-lock member on the base, the lock and the counter-lock members being coupled in correspondence of said closed position.

5. The apparatus according to claim 4, wherein each lock member comprises an elastically deformable flat wing having one end secured to the door and one end carrying a protrusion, in correspondence of said closed position the protrusion engaging a correspondingly shaped recess defined on the base.

6. The apparatus according to claim 4, wherein the holder also comprises a second sensor at least detecting when the closure element is in its closed position and emitting a corresponding closure signal, the control unit being connected to the second sensor and comprises a module for determining whether or not the closure element is in its closure position based on said closure signal emitted by the second sensor.

7. The apparatus according to claim 2, comprising:
   a treatment unit associated to the main support structure, the treatment unit having a semipermeable membrane dividing the treatment unit in at least a first chamber for the flow of blood which is in fluid communication with the cassette assembly and in a second chamber which has at least an outlet port in fluid communication with an outlet line,
   means for regulating a net flow of plasma water passing through the semipermeable membrane from the first to the second chamber and vice versa and wherein the apparatus comprises:
   a supply line for a treatment liquid, the supply line being connected at an inlet of the second chamber of the blood treatment unit, means for regulating a chemical composition of the treatment liquid in the supply line, the control unit also configured for controlling the means for regulating the chemical composition based on values taken by said calculated property.

8. The apparatus according to claim 7, wherein the emitter comprises a waves emitter emitting electromagnetic or acoustic waves with specified emission intensity and the detector comprises a detector of electromagnetic or acoustic waves which can detect a received intensity,
wherein the control unit is connected to the first sensor and to the regulating means, the control unit including:
a module for activating said first sensor to emit said signal and detect said return signal,
a module for calculating a property of a fluid circulating through the rigid tubular piece based on said emission and return signals, and
a module for controlling the regulating means based on values taken by said calculated property, the module for calculating a property of a fluid circulating through the rigid tubular piece includes:
a module for calculating a difference or a ratio between the emission intensity and the received intensity,
a module for determining an absorption of energy by the fluid circulating through the rigid tubular piece based on said difference or on said ratio,
a module for determining the property of the fluid circulating through the rigid tubular piece based on said absorption, the fluid being blood and the property of the fluid circulating through the rigid tubular piece including at least one selected in the group comprising:
blood density,
blood hematocrit,
blood hemoglobin concentration,
mean blood cellular volume.

9. The apparatus according to claim 1, wherein the seat comprises a first portion countershaped to the first end connector and a second portion countershaped to the second end connector, said first and second portions of the seat presenting a prismatic surface, the prismatic surface of at least one of said first and second portions bearing a radial recess which cooperates with a corresponding mating protrusion present on one of the end connectors.

10. The apparatus according to claim 9, wherein the prismatic surface of at least one of said first and second portions bears a radial protrusion which cooperates with the corresponding mating recess on one of the end connectors.

11. The apparatus according to claim 9, including a third sensor operatively associated to one of said first and second portions of the seat to detect the presence and proper position of the rigid tubular piece in the holder seat and emit a corresponding matching signal, and including a control unit connected to the third sensor and configured for determining whether the proper rigid tubular piece is in the right position within the seat based on said matching signal emitted by the third sensor, the third sensor being constructed to detect presence of a matching coupling between the protrusion on the end connector and the radial recess on the seat and to emit a corresponding matching signal.

12. The apparatus according to claim 11, wherein the control unit is configured for activating (i) the first sensor emitter to emit the signal and (ii) the first sensor detector to detect the return signal, and wherein the control unit comprises a module for commanding said activating only when the control unit positively concludes that the proper rigid tubular piece is in the right position within the seat, the control unit also configured for signaling that a fluid property cannot be calculated when the control unit has not positively concluded that the proper rigid tubular piece is in the right position within the seat.

13. A medical apparatus for an extracorporeal fluid treatment comprising:
a main support structure having at least a receiving portion and a holder,
a cassette assembly comprising:
a rigid casing defining at least a first fluid flow chamber, said casing also having an inlet to said first chamber and an outlet from said first chamber,
a first flexible tube having a first and a second end secured to the rigid casing to form a portion of a loop, the first end of the first flexible tube being connected to said first chamber outlet,
a second flexible tube having a first end connected to the inlet of said first chamber,
a third flexible tube having a first end secured to the rigid casing and in fluid communication with the second end of said first tube, characterized in that the cassette assembly further comprises:
a rigid tubular piece having:
a first end connector,
a second end connector, opposite said first end connector, and
an intermediate portion extending between said first and second end connectors for subjecting a fluid flowing through said intermediate portion to a measurement of at least a fluid parameter, the first end connector of the rigid tubular piece being secured to one selected in the group comprising: a second end of the second flexible tube, and a second end of the third flexible tube, the cassette assembly being mounted on the receiving portion carried by the main support structure,
at least a peristaltic pump carried by the main support structure and having a rotor, the portion of the loop of the cassette assembly receiving the rotor of the peristaltic pump,
the holder holding the rigid tubular piece of the cassette assembly, said holder comprising:
a base carried by the support structure and defining a seat for receiving at least the rigid tubular piece,
a first sensor and comprising at least an emitter of a signal and a detector which can detect a return signal;
a closure element which is coupled to the base and which is movable between a closed position, where the closure element closes the seat and secures in position the rigid tubular piece, and an open position, where the closure element leaves the seat open thereby allowing insertion or removal of the tubular piece into or from the seat, the closure element including a door hinged around a pivot axis on one side of the base, the door turning around said pivot axis when moving between said open and close positions, the door comprising at least one lock member cooperating with a counter-lock member on the base, the lock and the counter-lock member being coupled in correspondence of said closed position.

14. The apparatus according to claim 13, wherein the emitter and the detector are positioned in correspondence of said intermediate portion of the rigid tubular piece and wherein the emitter and the detector are positioned according to one of the configurations selected in the group comprising:
a configuration in which the closure element rigidly carries one of said emitter and detector, the base rigidly carrying the other of said emitter and detector,
a configuration in which the closure element rigidly carries both said emitter and detector, a configuration in which the base rigidly carries both said emitter and detector.

15. The apparatus according to claim 13, wherein the door comprises two lock members, one on each side cooperating with one respective counter-lock member on the base, the lock and counter-lock members being coupled in correspondence of said closed position.

16. A medical apparatus for an extracorporeal fluid treatment comprising:
   a main support structure including at least a receiving portion and a holder;
   a cassette assembly including:
      a rigid casing defining at least a first fluid flow chamber, said casing also having an inlet to said first chamber and an outlet from said first chamber,
      a first flexible tube having a first and a second end secured to the rigid casing to form a portion of a loop, the first end of the first flexible tube being connected to said first chamber outlet,
      a second flexible tube having a first end connected to the inlet of said first chamber,
      a third flexible tube having a first end secured to the rigid casing and in fluid communication with the second end of said first tube, and
      a rigid tubular piece including:
   a first end connector,
   a second end connector, and
   an intermediate portion extending between said first and second end connectors for subjecting a fluid flowing through said intermediate portion to a measurement of at least a fluid parameter, the first end connector of the rigid tubular piece being secured to one of: a second end of the second flexible tube, or a second end of the third flexible tube, the cassette assembly being mounted on the receiving portion carried by the main support structure; and
   at least a peristaltic pump carried by the main support structure and having a rotor, the portion of the loop of the cassette assembly receiving the rotor of the peristaltic pump, the holder holding the rigid tubular piece of the cassette assembly, said holder including:
      a base carried by the support structure and defining a seat for receiving at least the rigid tubular piece, and
      a first sensor and including at least an emitter of a signal and a detector which can detect a return signal,
      wherein the seat includes a first portion countershaped to the first end connector and a second portion countershaped to the second end connector, said first and second portions of the seat presenting a prismatic surface, the prismatic surface of at least one of said first and second portions bearing a radial recess which cooperates with a corresponding mating protrusion present on one of the end connectors.

17. The apparatus according to claim 16, wherein the prismatic surface of at least one of said first and second portions bears a radial protrusion which cooperates with the corresponding mating recess on one of the end connectors.

18. The apparatus according to claim 16, including a third sensor operatively associated to one of said first and second portions of the seat to detect the presence and proper position of the rigid tubular piece in the holder seat and emit a corresponding matching signal, and including a control unit connected to the third sensor and configured for determining whether the proper rigid tubular piece is in the right position within the seat based on said matching signal emitted by the third sensor, the third sensor being constructed to detect a presence of a matching coupling between the protrusion on the end connector and the radial recess on the seat and to emit a corresponding matching signal.

19. The apparatus according to claim 18, wherein the control unit is configured for activating (i) the first sensor emitter to emit the signal and (ii) the first sensor detector to detect the return signal, and wherein the control unit includes a module for commanding said activating only when the the control unit positively concludes that the proper rigid tubular piece is in the right position within the seat, and wherein the control unit is also configured for signaling that a fluid property cannot be calculated when the control unit has not positively concluded that the proper rigid tubular piece is in the right position within the seat.

* * * * *